US005599332A

United States Patent [19]

Cashel

[11] Patent Number: 5,599,332

[45] Date of Patent: Feb. 4, 1997

[54] PORTABLE RECEPTACLE FOR RECEIVING AND CONTAINING EMESIS

[76] Inventor: Karen A. Cashel, 1611 Diamond Dr., Newtown, Pa. 18940

[21] Appl. No.: 577,352

[22] Filed: Dec. 22, 1995

[51] Int. Cl.[6] .......... A61M 1/00

[52] U.S. Cl. .......... 604/317; 604/323

[58] Field of Search .......... 604/317, 323, 604/326, 327, 355; 128/760, 766, 771; 383/28, 35–36; 4/144.2, 144.3

[56] References Cited

U.S. PATENT DOCUMENTS

| | | | |
|---|---|---|---|
| Re. 29,321 | 7/1977 | Holbrook . | |
| 618,624 | 1/1899 | Stanek et al. . | |
| 3,646,935 | 3/1972 | Holbrook et al. . | |
| 3,797,734 | 3/1974 | Fleury et al. | 383/36 |
| 3,832,738 | 9/1974 | Kliemann . | |
| 3,920,179 | 11/1975 | Hall . | |
| 4,238,448 | 12/1980 | Salvadori et al. | 128/771 |
| 4,394,928 | 7/1983 | Philip . | |
| 4,930,997 | 6/1990 | Bennett . | |
| 4,950,247 | 8/1990 | Rosenblatt . | |
| 4,990,145 | 2/1991 | Fleury . | |
| 4,995,386 | 2/1991 | Ng . | |
| 5,045,076 | 9/1991 | Pierce . | |
| 5,049,273 | 9/1991 | Knox . | |
| 5,050,616 | 9/1991 | Wolff et al. . | |
| 5,062,835 | 11/1991 | Maitz et al. . | |
| 5,067,821 | 11/1991 | Young | 383/36 |
| 5,098,418 | 3/1992 | Maitz et al. . | |
| 5,112,322 | 5/1992 | Hathaway . | |
| 5,171,224 | 12/1992 | Tucker . | |
| 5,188,622 | 2/1993 | Müller et al. . | |
| 5,331,689 | 7/1994 | Haq | 128/760 |

OTHER PUBLICATIONS

Sporty's Pilot Shop, "Little John & Convenience Bag", p. 70, Nov. '95 –Feb. '96.

*Primary Examiner*—John G. Weiss
*Assistant Examiner*—David J. Cho
*Attorney, Agent, or Firm*—Sperry, Zoda & Kane

[57] ABSTRACT

A receptacle designed to aid in both the reception and the containing of emesis or vomit which significantly prevents spilling and splashing therefrom. The receptacle is portable and includes a main body defining an emesis containment chamber therein. A neck which includes a neck conduit extending therethrough is secured to an opening in communication with the emesis containment chamber to facilitate the flow of emesis therein. A mouthpiece means which is arcuate and is designed to universally abut the surrounding mouth area of a patient or user to further minimize any possibility of external splashing or leakage of emesis during use. A baffling device is included as well as optionally a one-way valve within the conduit defined in the neck to minimize back flow or splashing or spillage upwardly therethrough. Preferably a handle may be included including two handles which can be grasped by a user during use or which alternatively defined downwardly extending slots which can be secured to surrounding environmental structure such as bed rails to further aid retaining of the receptacle during usage. An auxiliary opening with detachable cap means therefore may be also defined in the main body of the receptacle. The neck and conduit are preferably oriented at an oblique angle with respect to the containment chamber to facilitate fluid movement therethrough and prevent back flow or back splashing.

18 Claims, 1 Drawing Sheet

PORTABLE RECEPTACLE FOR RECEIVING AND CONTAINING EMESIS

BACKGROUND OF THE INVENTION

1. Field of the Invention

The present invention deals with the field of devices utilized in the healthcare field generally for receiving bodily fluids. Devices for this purpose have been used primarily in hospitals but also in doctors' facilities and smaller clinics and the like. Currently, it is common to use basins, which are open, shallow, kidney-shaped, plastic pans for collection of bodily fluids, such as sputum and emesis. The present device is specifically usable for collecting of emesis. This is particularly important in view of disease control considerations, such as the likelihood that emesis might contain blood, which may present a risk of contamination by HIV, Hepatitis B, and/or nonbloodborne pathogens. As such, the present invention provides a unique configuration solely utilized for the purposes of safe and efficient gathering and containment of potentially dangerous spewed emesis.

2. Description of the Prior Art

Numerous prior art devices have been utilized for receiving and-containing fluids several of which are particularly useful in the healthcare field such as U.S. Pat. No. 618,624 issued Jan. 31, 1899 to L. Stanek et al on an "Antispilling Vessel"; and U.S. Pat. No. 3,646,935 issued Mar. 7, 1972 to L. Holbrook et al and assigned to Medical Development Corporation on "Fluid Collection Systems"; and U.S. Pat. No. 3,832,738 issued Sep. 3, 1974 to C. Kliemann and assigned to Kleen Test Products, Inc. on a "Mid-Stream Urine Collector"; and U.S. Pat. No. 3,920,179 issued Nov. 18, 1975 to K. Hall on a "Disposable Vomiting Bag"; and U.S. Re-Issue Pat. No. Re29,321 issued Jul. 26, 1977 to L. Holbrook and assigned to Medical Development Corporation on a "Fluid Collection Bottle And Improvements Therein"; and U.S. Pat. No. 4,394,928 issued Jul. 26, 1983 to M. Philip on a "Splash-Proof Container And Cover"; and U.S. Pat. No. 4,930,997 issued Jun. 5, 1990 to Alan N. Bennett on a "Portable Medical Suction Device"; and U.S. Pat. No. 4,950,247 issued Aug. 21, 1990 to R. Rosenblatt and assigned to Rosenblatt/IMA Invention Enterprises on an "Aspirator For Collection Of Bodily Fluids Including Improved Safety And Efficiency Elements"; and U.S. Pat. No. 4,990,145 issued Feb. 5, 991 to R. Fleury and assigned to GKR Industries, Inc. on a "Disposable Bag With Hand Protection"; and U.S. Pat. No. 4,995,386 patented Feb. 26, 1991 to R. Ng on a "Neonstal Mucus Extractor"; and U.S. Pat. No. 5,045,076 issued Sep. 3, 1991 to P. Pierce on "Disposable Insulated Surgical Basins"; and U.S. Pat. No. 5,049,273 issued Sep. 17, 1991 to S. Know on a "Suction Straining Apparatus"; and U.S. Pat. No. 5,050,616 issued Sep. 24, 1991 to A. Wolff et al and assigned to The U.S. of America as represented by the Secretary of the Department of Health and Human Services on a "Universal Collector For Submandibular-Sublingual Saliva"; and U.S. Pat. No. 5,062,835 issued Nov. 5, 1991 to C. Maitz et al on an "Aspirator Device For Body Fluids"; and U.S. Pat. No. 5,098,418 issued Mar. 24, 1992 to C. Maitz et al on an "Aspirator Device For Body Fluids"; and U.S. Pat. No. 5,112,322 issued May 12, 1992 to L. Hathaway on an "Emesis Head Appliance"; and U.S. Pat. No. 5,171,224 issued Dec. 15, 1992 to A. Tucker on "Protective Devices For Handling Body Fluid"; and U.S. Pat. No. 5,188,622 issued Feb. 23, 1993 to W. Muller et al and assigned to Genossenschaft Vego on a "Vacuum Bottle For Collection Of Body Fluids".

SUMMARY OF THE INVENTION

The present invention provides a portable receptacle for receiving and containing emesis which includes a main body member which preferably is mostly opaque and defines an emesis containing chamber therein. In order to determine the amount of fluid volume within the chamber which is often required by medical personnel, the main body member will also preferably include a translucent section for marking which includes a plurality of measurement indicia markings thereon to facilitate the measurement of the amount of total fluid volume within the emesis containment chamber at a given time.

Preferably the main body member of the portable receptacle also includes a side wall which defines a chamber opening therein in fluid flow communication with respect to the emesis containment chamber to facilitate flow of emesis thereinto and retaining therein. The main housing further preferably defines an exit opening therein in fluid flow communication with respect to the emesis containment chamber to further facilitate removal of material therefrom as used with certain configurations of the present design.

A neck is preferably included which defines a neck conduit extending therethrough with a neck inlet at one end of the neck conduit and a neck outlet at the other end of the neck conduit. The neck outlet is preferably attached with respect to the chamber opening defined in the side wall of the main body to facilitate fluid flow communication between the neck conduit and the emesis containment chamber. The neck preferably is attached to the side wall of the main body adjacent the chamber opening. The neck is preferably oriented at an oblique angle with respect to the side wall means of between 30 and 60 degrees to facilitate the flow of emesis through the neck conduit into the emesis containment chamber and to prevent spillage and splashing outwardly therefrom.

A mouthpiece may be also included in the design of the present invention which is attached with respect to the neck at the inlet thereof in order to facilitate positioning of the neck inlet adjacent to the mouth of a user for receiving emesis directly therefrom. This mouthpiece is preferably rotatably movable with respect to the neck in order to facilitate engagement thereof with respect to the mouth area of a patient. The mouthpiece includes an arcuate mouth engaging edge extending therealong to further facilitate engagement with the mouth area of the patient.

A baffle device is preferably positioned within the neck conduit defined in the neck to allow emesis to move thereby into the emesis containment chamber and to minimize spillage and leakage outwardly through the neck therefrom. The baffle device preferably includes a plurality of baffle plates positioned within the neck conduit and extending angularly downstream therewithin in order to facilitate control of splashing and/or spilling of emesis from the containment chamber. In order to further minimize splashing and spilling a mouthpiece cap may be included detachably positionable in engagement with the mouthpiece and adapted to extend thereover for selectively closing thereof to prevent emesis passing outwardly through the mouthpiece. Also a mouthpiece cap attachment line may be secured to the mouthpiece cap and attached to the neck in order to facilitate retainment of the mouthpiece cap with respect to the portable receptacle and minimize the chance of loss thereof during any extended time of non use.

A handle configuration may be secured to the main body member in order to facilitate holding and stabilizing thereof during usage of the portable emesis receptacle. The handle cooperates with the main body members in such a manner as to define at least one vertically extending slot to facilitate mounting of the portable receptacle as desired. This handle preferably includes a first handle member and a second handle member positioned oppositely with respect to one another on the main body in order to facilitate retaining of the portable receptacle as desired.

A one-way valve device may also be positioned within the neck conduit in such a manner as to facilitate control of the movement of emesis through the neck into the emesis containment chamber and to prevent spilling and splashing outwardly therefrom. An exit cap may also be included engageable with the exit opening of the main housing for selectively closing thereof such that the exit opening itself will only utilize when it is desired to empty the emesis containment chamber.

It is an object of the present invention to provide a portable receptacle for receiving and containing emesis where full containment of spewed emesis is made possible.

It is an object of the present invention to provide a portable receptacle for receiving and containing emesis wherein splashing of emesis during vomiting by a patient is minimized.

It is an object of the present invention to provide a portable receptacle for receiving and containing emesis wherein spillage of emesis during movement of the receptacle is prevented.

It is an object of the present invention to provide a portable receptacle for receiving and containing emesis wherein the receptacle which is provided for containing emesis is completely portable.

It is an object of the present invention to provide a portable receptacle for receiving and containing emesis wherein measurement of the amount of fluid loss during spewing of emesis can be accurately measured.

It is an object of the present invention to provide a portable receptacle for receiving and containing emesis wherein handles can be provided at central positions on both sides of an emesis container chamber to facilitate holding thereof.

It is an object of the present invention to provide a portable receptacle for receiving and containing emesis wherein handles are provided engageable with environmental structures such as bed rails of a standard hospital bed.

It is an object of the present invention to provide a portable receptacle for receiving and containing emesis wherein a neck is included for gathering of emesis which is angularly oriented with respect to the emesis containment chamber and the side walls of the body thereof.

It is an object of the present invention to provide a portable receptacle for receiving and containing emesis wherein an opaque main body is included for aesthetic reasons to minimize viewing of emesis located within the emesis containment chamber.

It is an object of the present invention to provide a portable receptacle for receiving and containing emesis wherein a translucent portion of the main body is defined adjacent to measurement indicia for determining total volume of fluid contained within the emesis containment chamber.

It is an object of the present invention to provide a portable receptacle for receiving and containing emesis wherein a one-way valve is provided for allowing receiving and retaining of emesis and preventing splashing and spillage therefrom.

It is an object of the present invention to provide a portable receptacle for receiving and containing emesis wherein a mouthpiece is provided for universal usage by any person.

It is an object of the present invention to provide a portable receptacle for receiving and containing emesis wherein a capping means is included for closing of the mouthpiece to minimize spilling of emesis from the portable receptacle after usage therein.

It is an object of the present invention to provide a portable receptacle for receiving and containing emesis wherein baffling means are provided to allow movement of emesis into the container and to prevent the movement of emesis exiting from the container unless desired.

It is an object of the present invention to provide a portable receptacle for receiving and containing emesis wherein rounded corners are provided at all edges of the main body to facilitate safety in usage thereof.

It is an object of the present invention to provide a portable receptacle for receiving and containing emesis wherein capital costs for the initial purchase of equipment is minimized.

It is an object of the present invention to provide a portable receptacle for receiving and containing emesis wherein maintenance requirements are minimized.

It is an object of the present invention to provide a portable receptacle for receiving and containing emesis wherein disease control is significantly enhanced.

It is an object of the present invention to provide a portable receptacle for receiving and containing emesis wherein the risks of contamination by nonbloodborne and bloodborne pathogens, including but not limited to HIV and Hepatitis B infected blood contained within emesis, is substantially reduced.

It is an object of the present invention to provide a portable receptacle for receiving and containing emesis wherein the use of an open top emesis containment basin is no longer necessary.

It is an object of the present invention to provide a portable receptacle for receiving and containing emesis wherein medical personnel is protected from disease contaminated blood and other body fluids often contained within emesis.

It is an object of the present invention to provide a portable receptacle for receiving and containing emesis wherein emesis can be fully gathered and contained despite the speed and volume of expulsion thereof.

It is an object of the present invention to provide a portable receptacle for receiving and containing emesis wherein safe and aesthetic collecting, handling and disposing of emesis is made possible.

It is an object of the present invention to provide a portable receptacle for receiving and containing emesis wherein a closed receptacle is provided which is portable to prevent direct skin contact by surrounding personnel including healthcare workers with possibly disease contaminated emesis.

It is an object of the present invention to provide a portable receptacle for receiving and containing emesis wherein an alternative exit aperture may be defined in the main housing.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

DETAILED DESCRIPTION OF THE PREFERRED EMBODIMENT

Figure 1:
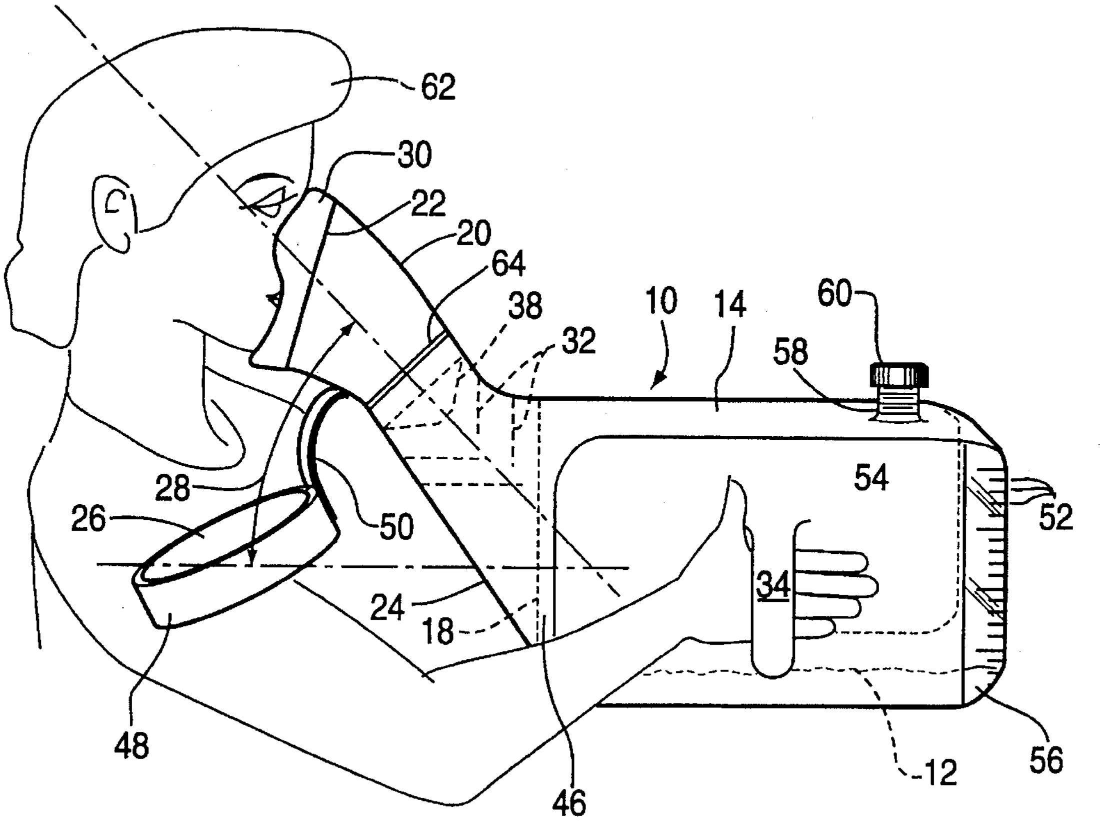
FIG. 1 is a front perspective illustration of an embodiment of the portable receptacle for receiving and containing emesis made in accordance with the present invention shown in usage by a patient or user.
Figure 2:
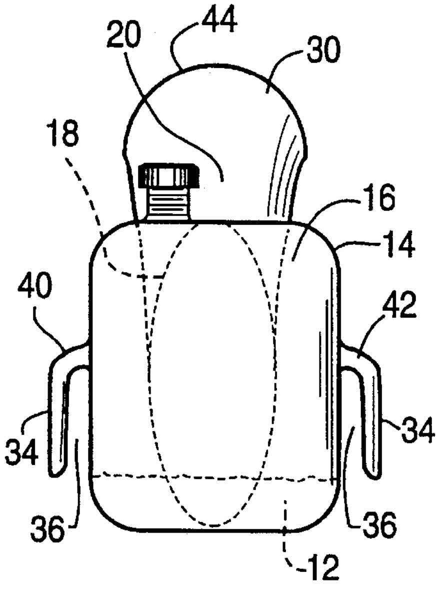
FIG. 2 is a side view of the embodiment shown in FIG. 1 taken from the right.
Figure 3:
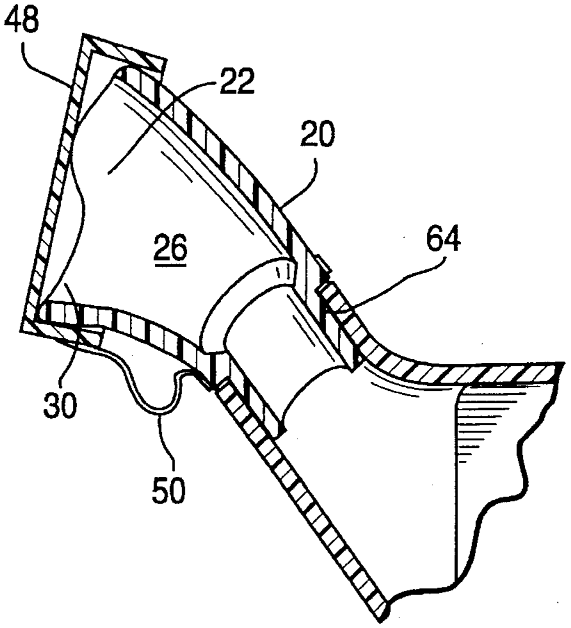
FIG. 3 is a side plan view of the neck piece and the mouth area of an embodiment of the present invention showing the mouthpiece cap in position extending over the mouthpiece area.

The present invention provides a new and useful improvement in gathering and disposing of emesis for use in hospitals, doctors' offices, clinics or even home environments. Numerous precautions are being published especially for use by healthcare workers as dictated by the Center For Disease Control to aid in the collection of various body fluids including emesis. Current disease control requirements, including preventative measures, have been significantly made more important by the significant presence of highly communicable diseases in society, such as HIV and Hepatitis B.

The present invention provides a portable receptacle 10 designed to accumulate emesis 12. Receptacle 10 includes a main body member 14 which defines an emesis containment chamber 16 therein. This emesis containment chamber 16 is designed to receive and contain emesis 12 and facilitate disposal thereof.

Main body member 14 defines a channel opening 18 preferably defined in a sidewall 46 thereof. This chamber opening 18 is in fluid flow communication with the emesis containment chamber 16 to facilitate the flow of emesis therein. A neck member 20 which preferably includes a neck conduit 26 extending therethrough from a neck inlet 22 to a neck outlet 24 is included in the apparatus of the receptacle 10. Neck member 20 is preferably at an angular orientation 28 of, preferably 30 to 60 degrees with respect to the main body member 14 and in particular with respect to the sidewall 46 thereof.

A mouthpiece 30 may be positioned over the neck inlet 22 to facilitate engagement thereof with respect to the mouth of a patient or user 62. Furthermore the mouthpiece 30 will preferably include an arcuate mouth engaging edge 44 adapted to contact the mouth area of the patient or user 62 in surrounding relationship to the user's mouth in order to facilitate receiving and containing of emesis 12 spewed therefrom.

The neck conduit 22 will preferably include baffle plates 32 positioned therein which are angularly oriented with respect to the neck conduit 26 such as to extend downstream therealong. The baffle plates 32 are designed preferably to allow emesis to be spewed from the neck inlet 22 through the neck conduit 26 to the neck outlet 24 and on into the emesis containment chamber 16 but to prevent similar reverse flow and thereby minimize spillage as well as minimizing any possibility of splashing. To further facilitate containment and prevent spillage and splashing a one-way valve 38 can optionally be included in the apparatus of the present invention. The one-way valve 38 is designed to allow emesis spewed through the neck conduit 26 at high speed to pass therethrough but to prevent reverse flow or reverse spillage outwardly through the neck conduit 26 from the outlet 24 to the inlet 22.

As an additional element of protection, a mouthpiece cap 48 may be positionable in engagement with the mouthpiece 30 to extend over the neck inlet 22 for closing thereof to prevent spillage of emesis 12 after usage of the portable receptacle 10. In order to prevent loss of the mouthpiece cap 48, a mouthpiece cap attachment line 50 may optionally be included which is attached with respect to the receptacle 10 and also with respect to the mouthpiece cap 48.

To facilitate holding of the receptacle 10 during usage, a handle means 34 may be included which may take the form of a first handle member 40 positioned on one side of the main body member 14 and a second handle member 42 positioned on the other opposite side of the main body member 14. In this manner a user can put his hands on both handles and rest the main body member 14 on his lap or abdomen for fixed holding thereof during the spewing of emesis 12.

Preferably the main body member 14 is generally opaque throughout in order to prevent direct viewing of the emesis 12 contained therein to make usage of the device more aesthetically pleasing. However, it is important under many circumstances that a doctor have an accurate measurement of the fluid volume of spewed emesis 12. For this reason the opaque areas 54 of the main body member 14 will preferably not include a section thereof positioned along the measurement indicia markings 52. This marking section 56 of the main body member 14 will preferably be defined as a translucent marking section to facilitate the viewing of the level of liquid within the emesis containment chamber 16 immediately adjacent the measurement indicia marking 52 to thereby determine the total fluid volume of spewed emesis 12.

The emptying of the emesis from the emesis containment chamber 16 can be achieved through the neck conduit 26 if desired. However, to further facilitate emptying of the containment chamber 16 an additional exit opening 58 may be optionally included with an exit cap member 60 engageable therewith for closing of the exit during usage and opening of the exit 58 whenever it is desired to empty the emesis containment chamber.

One of the unique aspects of the present invention is the orientation of the neck 20 and particularly the neck conduit 26 at an angle of 30 to 60 degrees with respect to the main body 14 and particularly with respect to the sidewall 46 thereof. This angular orientation when used in combination with the universal mouthpiece 30 allows usage by virtually any patient. Also, the downwardly extending baffle plates 32 allow movement of fluid into the emesis containment chamber 16 and prevent movement outwardly therefrom during the spewing of emesis 12 and thereafter during movement of the portable receptacle 10 to a disposal location. The transport of any filled container other than the receptacle 10 of the present invention to a location where it can be emptied is often difficult and risks contamination because of the numerous types of body fluids which are often contained with emesis 12 and therefore contained within the containment device. The apparatus of the present invention is small enough to be used in households as well as in ambulances and clinics and is certainly capable of being used in hospital and other similar environments.

While particular embodiments of this invention have been shown in the drawings and described above, it will be apparent, that many changes may be made in the form, arrangement and positioning of the various elements of the combination. In consideration thereof it should be understood that preferred embodiments of this invention disclosed herein are intended to be illustrative only and not intended to limit the scope of the invention.

I claim:

1. A portable receptacle for receiving and containing emesis comprising:

A. a main body member defining an emesis containment chamber means therein, said main body member defining an chamber opening means therein in fluid flow communication with respect to said emesis containment chamber means to facilitate flow of emesis thereinto;

B. a neck means defining a neck inlet means and a neck outlet means therein and a neck conduit means extending therethrough from said neck inlet means to said neck outlet means, said neck inlet means and said neck conduit means and said neck outlet means being in fluid flow communication with respect to one another, said neck outlet means being attached with respect to said chamber opening means defined in said main body member to facilitate fluid flow communication between said neck conduit means and said emesis containment chamber means, said neck conduit means being oriented angularly oblique with respect to said main body member to facilitate flow of emesis through said neck conduit means into said emesis containment chamber means;

C. a mouthpiece means attached with respect to said neck means at said inlet means thereon to facilitate positioning of said neck inlet means adjacent the mouth of a user for receiving emesis therefrom, said mouthpiece means being rotatably movably mounted with respect to said main housing means to facilitate engagement thereof with respect to the mouth of a patient;

D. a baffle means positioned within said neck conduit means defined in said neck means to allow emesis to move therethrough into said emesis containment chamber means and to minimize spillage and leakage outwardly through said neck conduit means from said emesis containment chamber means; and E. a handle means secured to said main body member to facilitate holding and stabilizing of said main body member during usage of the portable emesis receptacle.

2. The portable receptacle for receiving and containing emesis as defined in claim 1 wherein said baffle means comprises a plurality of baffle plates positioned within said neck conduit means and extending angularly toward said neck outlet means thereof to facilitate control of splashing and spilling outwardly from said emesis containment chamber means.

3. The portable receptacle for receiving and containing emesis as defined in claim 1 wherein said handle means cooperate with said main body member to define at least one vertically extending slot means to facilitate mounting of the portable receptacle.

4. The portable receptacle for receiving and containing emesis as defined in claim 1 wherein said handle means further comprises a first handle member and a second handle member, said first and second handle members being oppositely positioned on said main body member to facilitate mounting of the portable receptacle.

5. The portable receptacle for receiving and containing emesis as defined in claim 1 wherein said mouthpiece means includes an arcuate mouth engaging edge means therealong to facilitate engagement with the mouth area of a patient.

6. The portable receptable for receiving and containing emesis as defined in claim 1 further comprising an one-way valve means positioned within said neck conduit means to facilitate control of spilling and splashing from said emesis containment chamber.

7. The portable receptacle for receiving and containing emesis as defined in claim 1 wherein said main body member is at least partially opaque.

8. The portable receptacle for receiving and containing emesis as defined in claim 1 further comprising measurement indicia markings on said main body member to facilitate measurement of the amount of material within said emesis containment chamber means.

9. The portable receptacle for receiving and containing emesis as defined in claim 1 wherein said main housing means defines an exit opening means therein in fluid flow communication with respect to said emesis containment chamber means to selectively facilitate removal of material therefrom.

10. The portable receptacle for receiving and containing emesis as defined in claim 1 wherein said main body member includes a sidewall means with said chamber opening means being defined therein.

11. The portable receptacle for receiving and containing emesis as defined in claim 10 wherein said neck means is attached to said sidewall means of said main body member adjacent said chamber opening means, said neck means being oriented angularly oblique with respect to said sidewall means.

12. The portable receptacle for receiving and containing emesis as defined in claim 11 wherein said neck means is oriented at an angle of approximately 30 to 60 degrees with respect to said sidewall means.

13. The portable receptacle for receiving and containing emesis as defined in claim 1 further comprising a mouthpiece cap means detachably positionable selectively in engagement with said mouthpiece means and extending thereover for closing thereof to facilitate retaining of emesis within said emesis containment chamber of said main body member.

14. The portable receptacle for receiving and containing emesis as defined in claim 13 further comprising a mouthpiece cap attachment line means secured to said mouthpiece cap means and attached with respect to said neck means to facilitate retainment of said mouthpiece cap means with respect to the portable receptacle.

15. The portable receptacle for receiving and containing emesis as defined in claim 14 wherein said main body member includes a translucent section in the area adjacent to said measurement indicia markings to facilitate measurement of the amount of material within said emesis containment chamber means.

16. The portable receptacle for receiving and containing emesis as defined in claim 15 further comprising an exit cap means engageable with said main housing means extending over said exit opening means thereof for selective closing thereof.

17. A portable receptacle for receiving and containing emesis comprising:

A. a main body member being at least partially opaque and defining an emesis containment chamber means therein, said main body member defining an chamber opening means therein in fluid flow communication with respect to said emesis containment chamber means to facilitate flow of emesis thereinto;

B. a neck means defining a neck inlet means and a neck outlet means therein and a neck conduit means extending therethrough from said neck inlet means to said neck outlet means, said neck inlet means and said neck conduit means and said neck outlet means being in fluid flow communication with respect to one another, said neck outlet means being attached with respect to said chamber opening means defined in said main body member to facilitate fluid flow communication between said neck conduit means and said emesis containment chamber means, said neck conduit means being oriented angularly oblique with respect to said main body member to facilitate flow of emesis through said neck conduit means into said emesis containment chamber means;

C. a mouthpiece means attached with respect to said neck means at said inlet means thereon to facilitate positioning of said neck inlet means adjacent the mouth of a user for receiving emesis therefrom, said mouthpiece means including an arcuate mouth engaging edge means therealong to facilitate engagement with the mouth area of a patient;

D. a baffle means positioned within said neck conduit means defined in said neck means to allow emesis to move therethrough into said emesis containment chamber means and to minimize spillage and leakage outwardly through said neck conduit means from said emesis containment chamber means, said baffle means including a plurality of baffle plates positioned within said neck conduit means and extending angularly toward said neck outlet means thereof to facilitate control of splashing and spilling outwardly from said emesis containment chamber means;

E. a mouthpiece cap means detachably positionable in engagement with said mouthpiece means and extending thereover for selective closing thereof to facilitate retaining of emesis within said emesis containment chamber of said main body member;

F. a mouthpiece cap attachment line means secured to said mouthpiece cap means and attached with respect to said neck means to facilitate retainment of said mouthpiece cap means with respect to the portable receptacle; and G. a handle means secured to said main body member to facilitate holding and stabilizing of said main body member during usage of the portable emesis receptacle, said handle means cooperating with said main body member to define at least one vertically extending slot means to facilitate mounting of the portable receptacle as desired.

18. A portable receptacle for receiving and containing emesis comprising:

A. a main body member being at least partially opaque and including a translucent marking section thereon, said main body member defining an emesis containment chamber means therein, said main body member including a sidewall means, said sidewall means of said main body member defining an chamber opening means therein in fluid flow communication with respect to said emesis containment chamber means to facilitate flow of emesis thereinto, said main body member including measurement indicia markings on said translucent marking section thereof to facilitate measurement of the amount of material within said emesis containment chamber means, said main housing means further defining an exit opening means therein in fluid flow communication with respect to said emesis containment chamber means to selectively facilitate removal of material therefrom;

B. a neck means defining a neck inlet means and a neck outlet means therein and a neck conduit means extending therethrough from said neck inlet means to said neck outlet means, said neck inlet means and said neck conduit means and said neck outlet means being in fluid flow communication with respect to one another, said neck outlet means being attached with respect to said chamber opening means defined in said sidewall means of said main body member to facilitate fluid flow communication between said neck conduit means and said emesis containment chamber means, said neck means being attached to said sidewall means of said main body member adjacent said chamber opening means, said neck means being oriented angularly obliquely at approximately 30 to 60 degrees with respect to said sidewall means of said main body member to facilitate flow of emesis through said neck conduit means into said emesis containment chamber means;

C. a mouthpiece means attached with respect to said neck means at said inlet means thereon to facilitate positioning of said neck inlet means adjacent the mouth of a user for receiving emesis therefrom, said mouthpiece means being rotatably movable with respect to said main body member to facilitate engagement thereof with respect to the mouth area of a patient, said mouthpiece means including an arcuate mouth engaging edge means therealong to further facilitate engagement with the mouth area of a patient;

D. a baffle means positioned within said neck conduit means defined in said neck means to allow emesis to move therethrough into said emesis containment chamber means and to minimize spillage and leakage outwardly through said neck conduit means from said emesis containment chamber means, said baffle means including a plurality of baffle plates positioned within said neck conduit means and extending angularly toward said neck outlet means thereof to facilitate control of splashing and spilling outwardly from said emesis containment chamber means;

E. a mouthpiece cap means detachably positionable in engagement with said mouthpiece means and extending thereover for selective closing thereof to facilitate retaining of emesis within said emesis containment chamber of said main body member;

F. a mouthpiece cap attachment line means secured to said mouthpiece cap means and attached with respect to said neck means to facilitate retainment of said mouthpiece cap means with respect to the portable receptacle;

G. a handle means secured to said main body member to facilitate holding and stabilizing of said main body member during usage of the portable emesis receptacle, said handle means cooperating with said main body member to define at least one vertically extending slot means to facilitate mounting of the portable receptacle as desired, said handle means including a first handle member and a second handle member being oppositely positioned on said main body member with respect to one another to facilitate mounting of the portable receptacle;

H. an one-way valve means positioned within said neck conduit means to facilitate control of spilling and splashing from said emesis containment chamber; and I. an exit cap means engageable with said main housing means extending over said exit opening means thereof for selective closing thereof.

* * * * *